US007044000B2

(12) United States Patent
Feller

(10) Patent No.: US 7,044,000 B2
(45) Date of Patent: *May 16, 2006

(54) ULTRASONIC FLOW SENSOR USING QUASI-HELICAL BEAM

(76) Inventor: Murray F Feller, 21577 NW. 75th Avenue Rd., Micanopy, FL (US) 32667

( * ) Notice: Subject to any disclaimer, the term of this patent is extended or adjusted under 35 U.S.C. 154(b) by 0 days.

This patent is subject to a terminal disclaimer.

(21) Appl. No.: 11/161,135

(22) Filed: Jul. 25, 2005

(65) Prior Publication Data

US 2006/0059999 A1    Mar. 23, 2006

Related U.S. Application Data

(63) Continuation-in-part of application No. 10/946,834, filed on Sep. 22, 2004, now Pat. No. 6,973,842.

(51) Int. Cl.
*G01F 1/66*    (2006.01)

(52) U.S. Cl. .................. 73/861.27; 73/597; 73/610

(58) Field of Classification Search ................................ 73/861.26–861.29, 597, 598, 602, 610

See application file for complete search history.

(56) References Cited

U.S. PATENT DOCUMENTS

| | | | |
|---|---|---|---|
| 6,178,827 B1 | 1/2001 | Feller | |
| 6,370,963 B1 | 4/2002 | Feller | |
| 6,422,093 B1 | 7/2002 | Feller | |
| 6,457,371 B1 | 10/2002 | Feller | |
| 6,474,165 B1 * | 11/2002 | Harper et al. | ................. 73/623 |
| 6,508,134 B1 | 1/2003 | Feller | |
| 6,575,044 B1 | 6/2003 | Feller | |
| 6,584,860 B1 | 7/2003 | Feller et al. | |

OTHER PUBLICATIONS

Lynnwood, Lawrence C., Ultrasonic Measurements for Process Control, 1989, pp. 292-294 and related bibligraphic citations, Academic Press Inc., San Diego CA.

* cited by examiner

*Primary Examiner*—Harshad Patel
(74) *Attorney, Agent, or Firm*—David Kiewit

(57) ABSTRACT

A probe type acoustic transit-time flow sensor has paired transducers arranged to generate quasi-helical acoustic beams making a plurality of reflective contacts with a pipe's interior wall. The transducers in each pair are spaced apart along the flow axis so that transit-time measurements can be used both to measure the internal diameter of the pipe and to determine a flow rate. These measurements are combined to yield a volumetric flow rate. Various numbers of pairs of transducers can be put on a single probe or on multiple probes and used to provide a more accurate representation of a flow profile and therefore a more accurate volumetric flow determination.

22 Claims, 4 Drawing Sheets

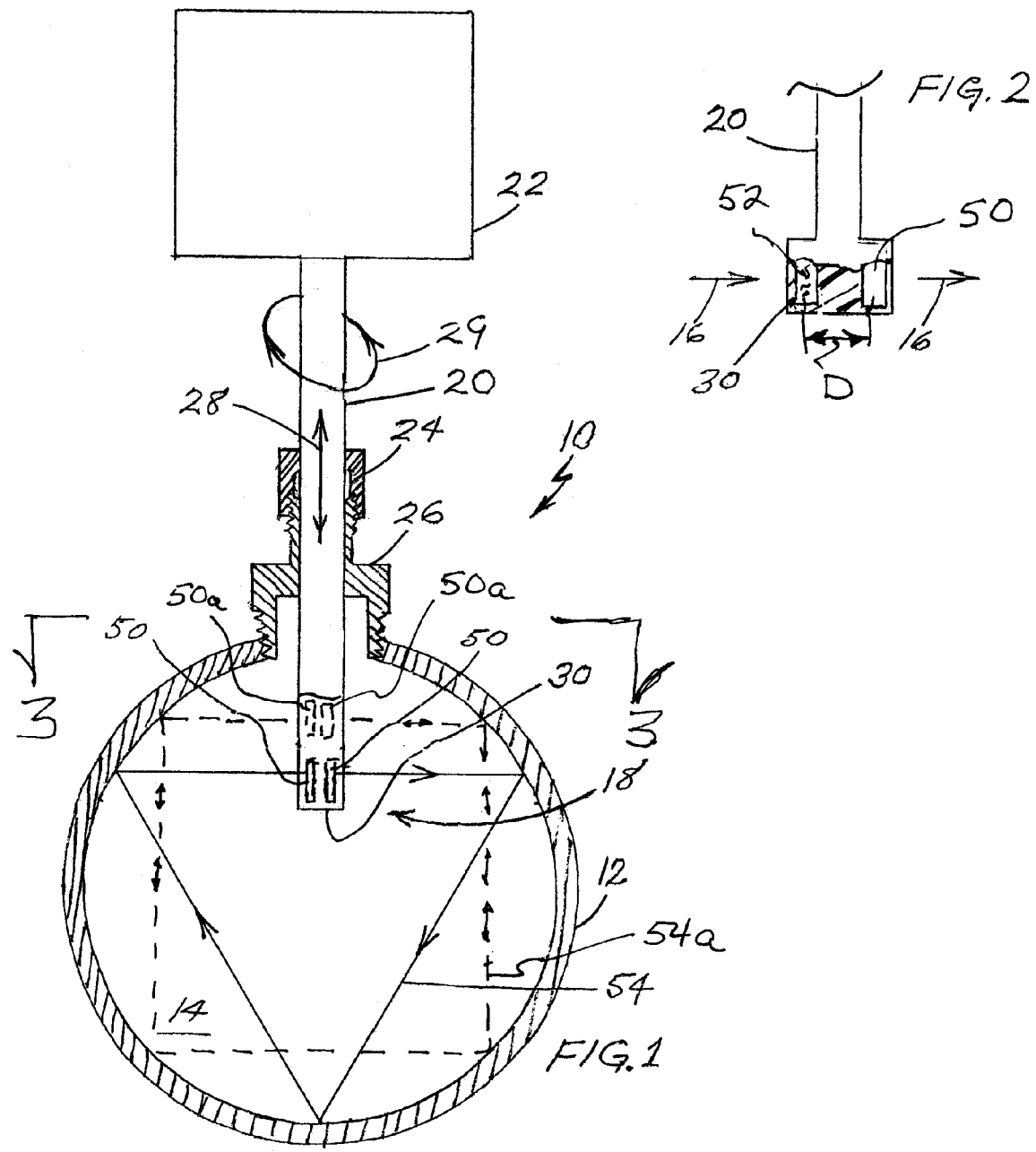

ULTRASONIC FLOW SENSOR USING QUASI-HELICAL BEAM

CROSS-REFERENCE TO RELATED APPLICATIONS

This application is a continuation-in-part of the inventor's U.S. Ser. No. 10/946,834, filed Sep. 22, 2004 and now issued as U.S. Pat. No. 6,973,842.

BACKGROUND OF THE INVENTION

The present invention relates to acoustic apparatus and methods for fluid flow measurement. More specifically, it relates to apparatus and methods for compensating for variations in the internal diameters of pipes in which flow is measured, for measuring flow in the presence of flow profile variations, for optimizing the location and orientation of a flow sensor and for detecting accumulation of pipe wall deposits.

Insertion probes for detecting the flow of fluids are typically mounted in round pipes having internal diameters that are not precisely known. Because these probes are generally used to measure flow rate by sampling a small portion of the flow profile and deriving from that measurement the volumetric flow rate based upon an assumed internal pipe diameter, a pipe diameter different from that assumed can introduce significant error into the derived results.

The magnitude of the problem can be seen by considering the ASTM A 106 dimensional limits for a range of diameters about a nominal diameter of six inches for Schedule 40 steel pipe. The tolerances are $+\frac{1}{16}"$, $-\frac{1}{32}"$ in diameter and $+15\%$, $-12.5\%$ in wall thickness. The corresponding variation in wetted cross sectional area approaches 2% and provides that degree of uncertainty in determining volumetric flow rate. Those skilled in the art will recognize that tolerances vary with the pipe size and may increase or decrease from the recited example.

The potential error related to this variation in internal diameter has not received much attention in the past because of the acceptance of the probe type of sensing instrument as one of relatively low accuracy and because of the difficulty in measuring the internal diameter of installed pipes. There is, however, an increasing demand for improved performance, which indicates that a practical means of compensation for diameter variations is desired.

Insertion probes generally need to be inserted to a correct depth and to have a precise angular orientation with respect to the direction of the flowing fluid in order to minimize flow measurement error. Feldman et al., in U.S. Pat. No. 6,584,860, the disclosure of which is herein incorporated by reference, teach methods of and apparatus for measuring a distance between a portion of the piping apparatus into which a probe is inserted, as well as for combining the results of these measurements with a presumed pipe diameter in order to insert the probe to the correct depth.

Accumulation of scale and other deposits on the inside walls of pipes through which fluids flow can significantly change the effective diameter of the pipes and can also inhibit flow near the pipe walls so as to cause a change in the flow profile. This is a recognized problem that is not solved by the prior art, which ignores diameter changes and uses a single, preset diameter throughout the service life of a given flow sensor.

Acoustic flow sensing probes using time-of-flight technologies as exemplified in my U.S. Pat. Nos. 6,370,963, 6,422,093, 6,457,371, 6,508,134, 6,178,827 and 6,575,044, the disclosures of which are herein included by reference, teach means for measuring fluid flow rates which are compatible with the present invention.

BRIEF SUMMARY OF THE INVENTION

My parent U.S. Pat. No. 6,973,842 addresses the above issues, the disclosure thereof being herein incorporated by reference. The present invention expands on that art and further integrates it with the acoustic flow sensing means. My patent U.S. Pat. No. 6,457,371 is also particularly applicable for flow sensing operation with the present invention.

In an embodiment of the present invention, a probe type acoustic time-of-flight (also known as transit-time) flow sensor comprises a transmitting transducer arranged to generate an acoustic beam directed so as to make a plurality of reflective contacts with the pipe's interior wall prior to reaching a receiving transducer displaced along the flow axis from the transmitting transducer. This displacement enables a flow rate related time measurement to be made and provides an improvement over what is taught in my cited parent application. The preferred transducers may periodically exchange functions or may concurrently be in the transmitting and receiving modes to measure a differential acoustic transit-time between the upstream and downstream acoustic signals and therefore the flow rate. Each of the preferred transducers is aimed to project an acoustic energy beam at an angle which crosses the flow axis so that, after being reflected by the pipe walls, the beam can be received by another transducer. The acoustic energy paths between a pair of transducers thus define two quasi-helices, one in each direction.

The acoustic energy paths, when projected onto a cross-section perpendicular to the axis of the pipe, approximate chordal paths. In a preferred embodiment of the present invention, where the insertion depth of the transducers is 25% of the pipe's diameter and the transducers are beamed horizontally, these paths define a quasi-helix that appears, in cross-section, like an equilateral triangle. That is, the path can conceptually be constructed by drawing an equilateral triangle, cutting through one vertex and then moving the cut ends of the triangle apart along a line perpendicular to the plane of the triangle by a selected amount corresponding to a flow measurement distance between the two transducers. The associated transit time is responsive to the flow rates along those paths and the fluid flow intersecting those paths provides an approximation of the volumetric flow in the entire pipe. Hence, the volumetric accuracy is improved. Further improvement is possible when more than one probe is used and is particularly effective when the respective associated acoustic energy paths have different locations in the pipe cross-section. Such improvement is particularly evident when the flow profile is not uniform.

The acoustic transit time is proportional to the internal diameter ("ID") of the pipe, thereby allowing the pipe ID to be determined and flow rate adjustments to be made based upon the measured pipe ID. The adjustment may be a manual or automatic adjustment of the flow sensor's span calibration.

The magnitude of the received acoustic signal is an indication of the optimization of the acoustic path and possible presence of scale or other deposits. When the probe is adjusted to optimum insertion depth and rotational orientation angle, the signal has a maximum level. By adjusting the probe mounting during its installation for this maximum level, an installation is made to more closely approximate the factory calibration conditions than that which would result if the installer merely used relatively crude mechanical measurements and his visual aiming abilities to set depth and angle. To facilitate this calibration, the flow sensing probe may contain a display such an analog or digital voltmeter or array of LEDs to indicate the received signal level.

Although it is believed that the foregoing recital of features and advantages may be of use to one who is skilled in the art and wishes to learn how to practice the invention, it will be recognized that the foregoing recital is not intended to list all of the features and advantages of the invention, and that less than all of the recited features and advantages may be provided by some embodiments.

BRIEF DESCRIPTION OF SEVERAL VIEWS OF THE DRAWING

The various advantages of the present invention will become apparent to one skilled in the art by reading the following specification and subjoined claims and by referencing the following drawings in which:

FIG. 1 is a partly schematic, partly sectional view taken perpendicular to the axis of the pipe of a preferred embodiment of a flow rate measuring insertion probe inserted through a fitting on an upper surface of a pipe.

FIG. 2 is a detailed partly cut-away view of the probe of FIG. 1 taken along the axis of the pipe.

DETAILED DESCRIPTION OF THE INVENTION

Figure 3:
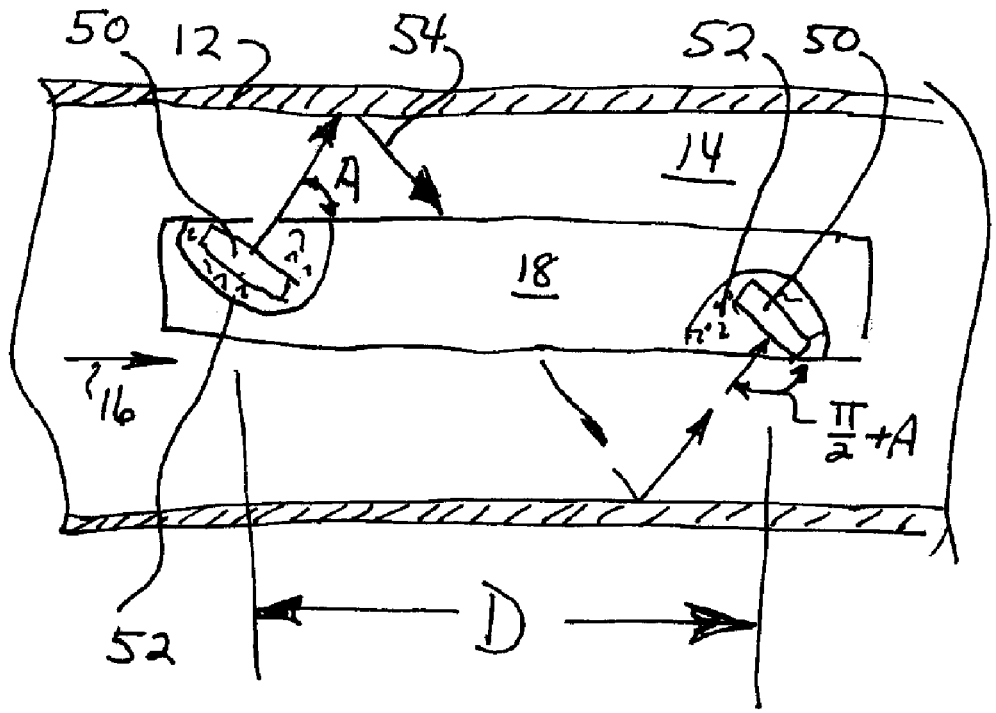
FIG. 3 is a horizontal sectional view of the probe of FIG. 1, as indicated by the arrows 3—3 in FIG. 1.

In studying the detailed description, the reader may be aided by noting definitions of certain words and phrases throughout this patent document. Whenever those definitions are provided, those of ordinary skill in the art should understand that in many, if not most instances, such definitions apply to both preceding and following uses of such defined words and phrases. At the outset of this Description, one may note that the terms "include" and "comprise," as well as derivatives thereof, mean inclusion without limitation; and the term "or," is inclusive, meaning and/or.

The term "insertion probe" as used herein, denotes an item elongated along a probe axis and designed to be inserted into a pipe or other vessel so that a sensing element on, or closely adjacent, the inserted end of the probe is at a selected probe axial insertion depth and orientation with respect to that pipe or vessel. Although much of the ensuing discussion is directed toward in-field insertion of probes into a pre-existing pipe, it will be understood that an insertion probe could equally well be factory-installed in a pipe section that was then built into a run of piping. A "flow probe", as used herein, provides the conventional denotation of a portion of a flow sensor configured to be inserted into a pipe. When a flow probe is inserted into a pipe so that a flow measurement direction, defined with respect to the probe, and perpendicular to the probe axis, is parallel to or collinear with the axis of the pipe, a raw flow signal from the flow probe is then a measure of the rate at which the fluid is flowing past the probe in the immediate vicinity of the probe at whatever insertion depth has been selected. In many cases what is desired is the volumetric flow rate (e.g., gallons per minute flowing through the pipe), which is calculated by multiplying a representative fluid flow rate by the cross-sectional area of the inside of the pipe. Thus a "volumetric flow sensor" is an instrument providing an output signal value representative of the volumetric flow rate, which may be described as a respective volumetric flow rate when derived from phase changes in upstream and downstream acoustic transmissions between a pair of transducers, or which may be referred to as a composite volumetric flow rate when generated by combining (e.g., by averaging) measurements made using multiple pairs of transducers. Prior art volumetric flow sensors generally operate by assuming a nominal value for the inside diameter of a pipe and using that value to calculate the cross-sectional flow area, a practice which often introduces serious errors as the ID assumptions are often incorrect.

The ensuing disclosure will describe apparatus operated to define acoustic beams traveling along a path comprised of straight line segments skewed with respect to the pipe axis. Those versed in geometry will appreciate that in a limiting situation in which the individual straight line segments have infinitesimal length the path becomes a helix. Hence, acoustic paths described herein will be referred to as having a quasi-helical shape. These quasi-helical acoustic beams are sometimes described as being propagated transverse to the pipe axis from a transducer. The reader will appreciate that in this context 'transverse' describes both beams having a center line perpendicular to the pipe axis and beams that are slightly angled away from the perpendicular so that the center line of the beam extends between two transducers that are spaced apart along the pipe axis.

In large pipes having a smooth inside surface one commonly finds that a flow velocity detector inserted to 11% of the ID of the pipe will provide a representative raw flow signal output value usable for determining volumetric flow over a wide range of flow rates. If one is dealing with smaller pipes or with pipes having a rough internal surface, a somewhat deeper insertion depth is typically desired for best volumetric accuracy. Thus, regardless of what insertion depth is nominally selected, it will be understood that installation of a flow probe comprises both inserting the probe to a selected insertion depth and assuring that the predetermined flow measurement direction is parallel to the pipe axis. Furthermore, these insertion depths assume a typical flow velocity profile through the pipe as is found when there is a length of straight pipe, both upstream and downstream of the flow sensor location, that is much greater than the pipe diameter, or when aggressive flow conditioning methods are used to achieve the same result. This can cause a problem in that many applications require the sensor be located close to an elbow, valve or branched connection which, over a range of fluid velocities, can so distort the velocity profile at the flow sensor location as to make the measurement useless.

Turning now to FIG. 1, one finds an acoustic time-of-flight flow insertion probe sensor 10 in accordance with a preferred embodiment of the present invention as it would be mounted in a pipe 12 containing a fluid 14 flowing along the pipe axis, which is perpendicular to the plane of FIG. 1 and which is indicated with the arrow 16 in other figures. As is conventional in the use of insertion probes, the depicted sensing head 18 is supported by a hollow stem 20 serving as a conduit for wires (not shown) coupling the transducers 50 to associated circuitry 22.

During installation of a preferred probe sensor 10 the shaft seal 24 of a conventional insertion fitting can be loosened to allow an operator to move the stem 20 into and out of the pipe, as depicted by the double-headed arrow 28, and to rotate the stem about its axis, as depicted by the double headed arrow 29, into a selected setting. As will be discussed in greater detail later hereinafter, these adjustments can assure that the sensing head 18 is disposed at a desired insertion depth and that the flow measurement direction is parallel to or coincident with the flow axis 16. Those skilled in the flow measurement arts will recognize that many mechanisms and approaches can be used to adjust both the depth and the rotational settings.

A preferred sensing head 18 comprises a pair of piezoelectric transducers 50 mounted in a suitable support 30 and aimed transverse to the pipe axis through the fluid 14 at an inner surface of the pipe 12. At a depth of 25% of the pipe's diameter the acoustic path, depicted by the solid arrowed lines 54, forms a quasi-helix having three equal legs that, when viewed in the cross-sectional view of FIG. 1, appears to be an equilateral triangle. The transducers 50 may be oriented other than horizontally and the head 18 positioned at different depths to enable probe operation with other acoustic paths. For example, transducers 50a oriented horizontally and located at an insertion depth of 13.3% of the pipe ID, produce a four reflection quasi-helical path that appears as a square in the view of FIG. 1, as indicated by the dashed arrowed lines 54a. Those skilled in the acoustic arts will recognize that although a real acoustic beam would have an angular dispersion about a center line, in the interest of clarity of presentation only the center line of the beam is depicted in the drawing.

Although one of the motivations for the present invention was to reduce the component count and complexity from what is shown in the captioned parent application, a single sensor head 18 of the invention may optionally be provided with two pairs of transducers 50, 50a spaced apart along the probe axis, each pair having its own associated acoustic path 54, 54a that can be used for measuring both the pipe ID and a respective volumetric flow rate. This approach allows for measurements to be made using additional acoustic paths that sample different portions of the overall flow profile and that can thus improve the overall accuracy of measurement when the respective diameter and volumetric flow rates are averaged, or otherwise combined, to yield a single, composite measurement of volumetric flow rate. Moreover, this approach provides redundancy which may offer increased system reliability.

Figure 5:
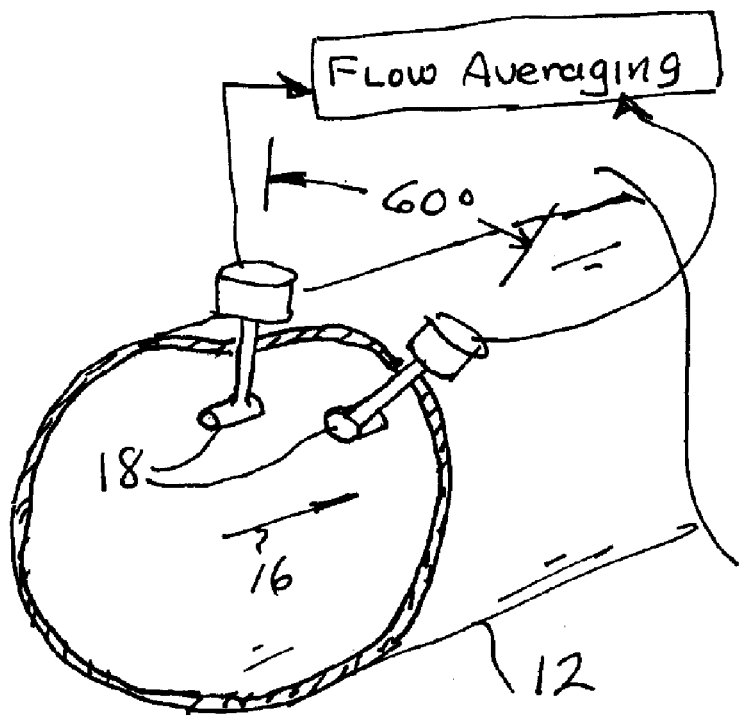
FIG. 5 is a partly schematic, partly cut-away view of an embodiment of the invention employing two flow probes oriented at different angular settings with respect to the flow axis.
Figure 6:
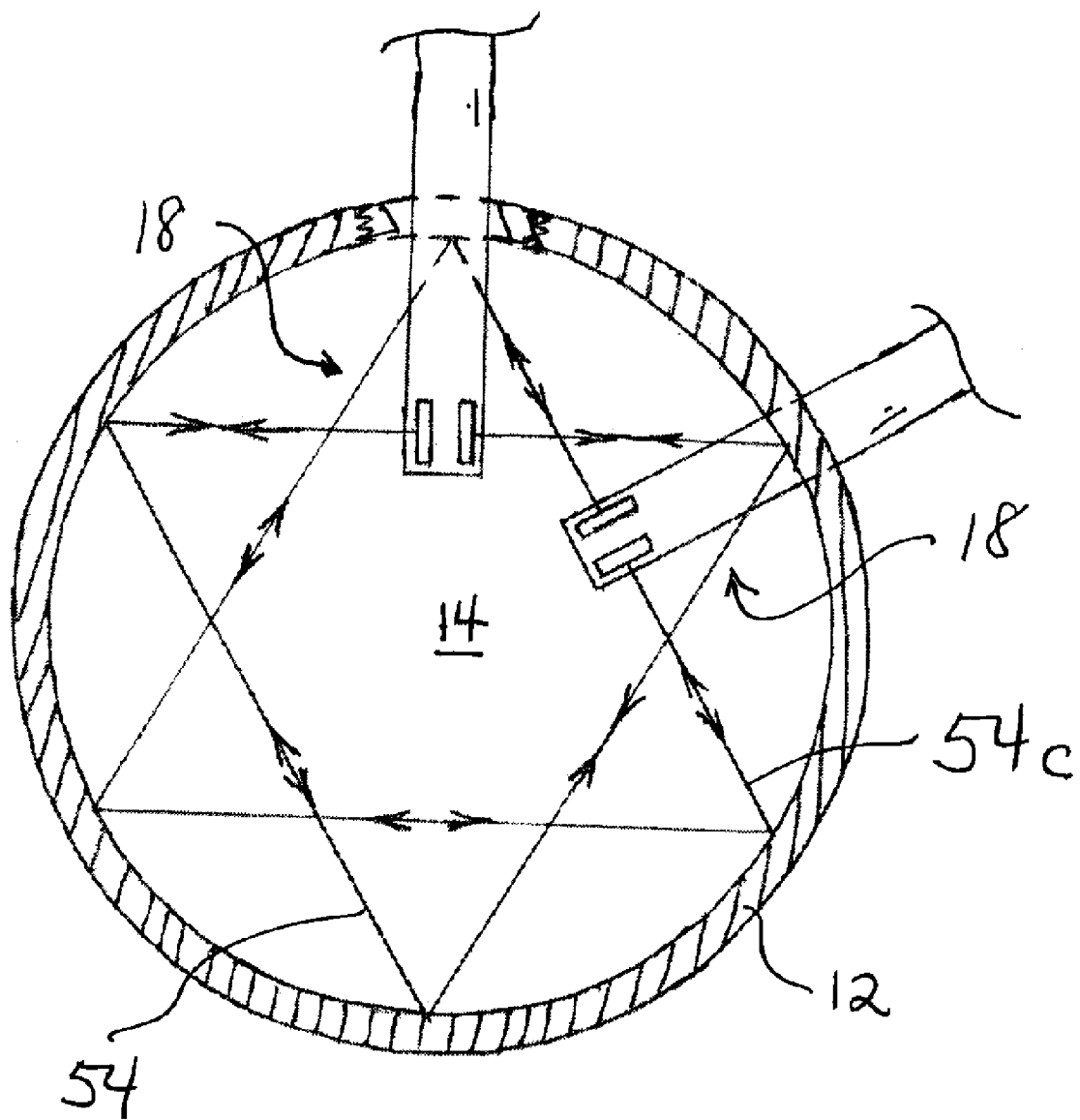
FIG. 6 is a partly schematic, partly sectional view taken perpendicular to the axis of the pipe of the embodiment of FIG. 5.

As an alternative to the approach depicted in FIG. 1 of spacing pairs of transducers along the axis of a single probe, one can also, as depicted in FIG. 5 and FIG. 6, employ multiple probes, where each probe axis has a respective angular setting with respect to the flow axis and where the probes are optionally spaced out along the pipe axis by selected probe-to-probe spacings. In arrangements of this sort each of the probes comprises a respective sensing head having at least one pair of transducers mounted on it in order to sample respective portions of the overall flow. In a preferred embodiment depicted in FIG. 6, each of the two sensing heads 18 generates a respective three-segment acoustic beam 54, 54c. These beams are separated by sixty degrees of arc about the flow axis, where the projected acoustic paths trace out a familiar Jewish star. There is, of course, no requirement for having nearly identical acoustic paths generated at each of the probes. One could, for example, use different insertion depths for each of two probes so that the first probe generated at three-segment quasi-helix and the second generated a four-segment quasi-helix. Moreover, the use of multiple probes spaced out along the flow axis does not preclude the use of additional pairs of transducers spaced apart along the probe axis of one or more of the probes. In order to prevent interference between pairs of transducers in an arrangement of this sort, one may space each probe out from the other probes along the pipe axis.

A flow measurement direction spacing, denoted as D, between the two transducers 50 in a pair thereof lies along the axis of flow when the probe is properly oriented. This ensures that the acoustic paths of interest are quasi-helices, and do not lie in a single plane. This flow measurement direction spacing is, of course, essential in order to enable a differential transit-time measurement of flow rate to be made. The transducers, particularly for small pipe sizes, may be angled off the exact perpendicular to the pipe axis in order to maximize the acoustic transmission along the lines 54 between the transducers. In the depiction of FIG. 3, one of the transducers is set to transmit and receive along a beam making an acute angle A with the flow measurement direction and the other of the transducers is set to transmit and receive along a beam making an obtuse angle (that is ninety degrees of arc greater than A) with that direction. Because the acoustic beams have an angular dispersion—i.e., are typically cones rather than straight lines—in some situations one may choose to set the transducers perpendicular to the flow measurement direction and select the flow measurement direction spacing and the angular dispersion so that off-axis components of the acoustic beams can propagate between the separated pair of transducers.

The transducers, as illustrated in FIG. 3, are preferably backed or partially surrounded by known acoustic isolation materials 52 such as a polymeric foam or a resonating material in order to minimize undesired acoustic radiation and reception.

During exemplary operation, the transducers 50 concurrently transmit and receive short bursts of acoustic energy consisting of sixteen cycles of a 4 MHz signal along the multi-segment acoustic path lines 54. When placed in a pipe full of fluid, the acoustic beams are reflected multiple times from the internal surface of pipe 52 to define the complete acoustic path between the transducers from which one can immediately derive the transit time, from which the corresponding internal pipe diameter can be determined. The cyclic signals representative of the bursts of acoustic energy are also phase compared, as is known in the art of transit-time flow meters, in order to derive the time difference between them from which fluid flow rate is determined.

The arrangements described above operate for selected combinations of transducer angles, rotational settings of the probe stem, insertion depths and pipe sizes and depend on these parameters being chosen so as to form a quasi-helical acoustic path having a quasi-helix axis parallel to or along the axis of the pipe. If the probe stem is at an incorrect angular setting the acoustic beams will generally follow an undesired path, so that a beam from one of the transducers is not received by the other. Correspondingly, if the insertion depth is slightly different than the selected one, the multiply reflected acoustic beams will largely miss the receiving transducer or transducers. The reader should recognize that there may be more than one insertion depth within a pipe at which a readily detectable signal will be found.

The requirement for precise positioning is a positive aid during installation of a sensing head of the invention. As the probe approaches the optimum location in both depth and rotational angle with respect to the central axis of the pipe, the magnitude of the received acoustic signals rapidly increases. The rate of change of these signals depends on several factors such as the beam angles, transducer alignment and condition of the pipe's reflective surface. In an implementation of the invention where the probe transducers were 0.200" wide, 0.125" high and 0.020" thick, and the probe was located in a circular section simulating a pipe having an eight inch ID, a probe insertion depth differing by about 0.050" from the optimum depth produced a received acoustic signal variation of 50%, thus providing the installer with a usable insertion depth tolerance value. A probe rotation of about 5 degrees from the optimum alignment with the central axis of the pipe also produced a received acoustic signal variation of 50%, similarly providing the installer with a rotational tolerance value. This order of sensitivity to mechanical positioning of the probe is, from the perspective of personnel installing the probe, a good balance for locating the approximate insertion position and then making fine adjustments for its optimization.

Figure 4:
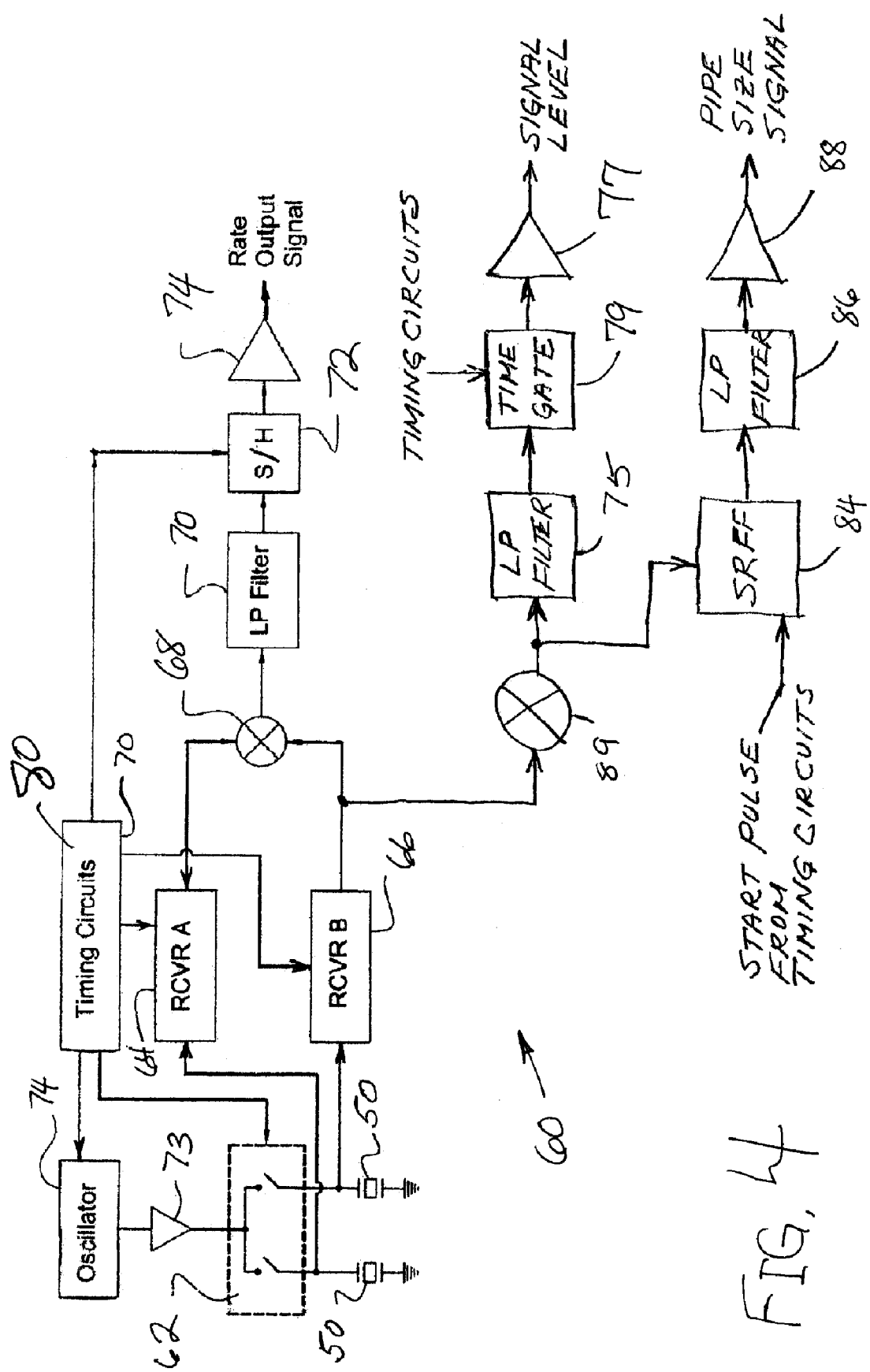
FIG. 4 is a simplified block diagram of a circuit usable with the apparatus of FIGS. 1–3 for aiding installation, measuring pipe diameter, and measuring flow.

Turning now to FIG. 4, one finds a block diagram of a simplified exemplary signal processing circuit 60 using the principles of both ultrasonic time-of flight flow rate detection and distance detection for the present invention. One portion of the circuit is used to provide a flow rate signal on an ongoing basis. Another portion is used to determine the actual pipe size. A third portion is used to determine optimal rotation of the probe about its axis and to set the probe to its desired depth.

In the depiction of FIG. 4, an oscillator 74 produces bursts of continuous high frequency waves which are isolated by buffer 73 and supplied to a two-pole switch 62 connected to transducers 50. Each transducer is also connected to a respective receiver 64,66, which provide two input signals to a phase detector 68 whose output passes through a low pass filter 70 to a sample and hold circuit 72 and finally to an output amplifier 74, which provides the flow rate output signal. A detailed description of this portion of the circuit operation is found in my patent U.S. Pat. No. 6,457,371.

The output signal from one of the receivers 66 is also provided to an amplitude detector 89, is filtered by a low-pass filter 75 and passes through the time gate 79 to a signal level output amplifier 77 which provides the installation circuit output signal. The output from amplitude detector 89 is also routed to an SR-type flip flop 84, as is the start pulse from the timing circuits 80. The output from the flip flop 84 passes through a low pass filter 86 to a size signal output amplifier 88 which provides the pipe size signal. A more detailed description of this portion of the circuit operation is found in my parent patent application Ser. No. 10/946,834.

Those skilled in the transit-time measurement arts will appreciate that although the preferred circuit operates both transducers simultaneously, one could also choose to operate the transducers in an alternating mode having a first phase in which a first transducer transmitted while the second received and a second phase in which the second transmitted and the first received. Moreover, those skilled in the art will recognize that in cases where measurements from more than one pair of transducers are used to yield a single composite value of volumetric flow, the logical and mathematical processes that yield the composite value can be carried out in a number of known ways and may involve a wide variety of combinations of dedicated electronic hardware or general purpose electronic hardware operating under control of suitable software.

Preferred embodiments of the invention are used to assist in the installation of the probe, to measure both a raw flow signal value and a pipe size signal value, and to then employ a suitable flow measurement circuit means to calculate a volumetric flow output from the raw flow and size data. Although this approach is generally preferred, the reader will note that in some circumstances in which the pipe ID is known with acceptable accuracy beforehand, one could store a value of the pipe size signal (e.g., as a datum in a computer memory or as a manual calibration setting of a potentiometer) and a flow measurement circuit could receive that stored value and use that stored value in conjunction with one or more raw flow signals to calculate a volumetric flow rate. Those skilled in electronics will recognize that there are many possible ways to provide these calculations and that the flow measurement circuitry may comprise, without limitation, general purpose digital microcomputers and purpose-built analog circuitry.

Although the present invention has been described with respect to several preferred embodiments, many modifications and alterations can be made without departing from the invention. Accordingly, it is intended that all such modifications and alterations be considered as within the spirit and scope of the invention as defined in the attached claims.

What is claimed is:

1. A flow sensor for measuring a volumetric flow rate of a fluid flowing in a pipe, the sensor comprising: at least one probe having a respective axis and insertable into the pipe to a respective insertion depth, each at least one probe respectively comprising at least one pair of acoustic transducers spaced apart by a respective flow measurement distance along a respective flow measurement direction transverse to the respective probe axis and arranged to transmit and receive respective oppositely directed acoustic signals transverse to the respective flow measurement direction; at least one signal processing circuit for energizing at least one pair of transducers associated therewith, for receiving respective transit-time signals from those transducers and for generating therefrom at least one raw flow signal output responsive to a component of the fluid flow along the respective flow measurement direction; and a flow measurement circuit operable to receive a size signal value representative of an inside diameter of the pipe and the at least one electrical flow signal output and to calculate therefrom the volumetric flow rate.

2. The flow sensor of claim 1 wherein the signal processing circuit is also operable to generate the size signal value.

3. The flow sensor of claim 1 wherein the at least one probe is rotatable about the respective probe axis so that the respective flow measurement direction is aligned with an axis of the pipe.

4. The flow sensor of claim 1 wherein each at least one signal processing circuit further respectively comprises at least one time-gate switching element operable to prohibit processing of the transit-time signals unless the associated probe is inserted to within an insertion depth tolerance value of the respective insertion depth, and the respective flow measurement direction is aligned with an axis of the pipe within a rotational tolerance value.

5. The sensor of claim 1 comprising two pairs of transducers associated with a single probe, the two pairs spaced apart along the probe axis by a selected spacing.

6. The sensor of claim 5 wherein the respective insertion depth and the selected spacing are selected so that when the first pair of transducers is energized they define a first acoustic beam reflected from the pipe at three respective locations and so that when the second pair of transducers is energized they define a second acoustic beam reflected from the pipe at four respective locations.

7. The sensor of claim 1 comprising two pairs of transducers, each of the two pairs mounted on a respective probe having a respective angular setting with respect to the axis of the pipe.

8. The flow sensor of claim 1 wherein each transducer is arranged to transmit and receive a respective acoustic signal perpendicular to the associated flow measurement direction, wherein each acoustic signal is characterized by a beam dispersion and wherein at least the beam dispersion and the respective flow measurement direction spacing are selected so that the respective acoustic signal transmitted from any one of the transducers is received by the other transducer with which it is paired when the sensor is installed in the pipe and the fluid is flowing.

9. The flow sensor of claim 1 wherein one of the transducers in each at least one pair thereof is arranged to transmit and receive a respective acoustic signal at an acute angle to the respective flow measurement direction and that transducer with which it is paired is arranged to transmit and receive a respective acoustic signal at an obtuse angle that is ninety degrees of arc greater than the acute angle to the respective flow measurement direction.

10. A method of measuring a volumetric flow rate in a pipe having a pipe axis, the method comprising the steps of: a) providing at least one probe having a respective probe axis, each at least one probe respectively comprising at least one pair of acoustic transducers spaced apart by a respective flow measurement distance along a respective flow measurement direction transverse to the respective probe axis and arranged to transmit and receive respective oppositely directed acoustic signals transverse to the flow measurement direction and at least partially along the axis of the pipe; b) inserting the at least one probe into the pipe so that its respective flow measurement direction is parallel to the axis of the pipe and so that a respective quasi-helical beam extends between each pair of transducers, the respective beam reflected a respective selected number of times, the respective selected number being at least three, from an inside surface of the pipe; c) calculating, from a diameter of the pipe and a respective measured phase change in acoustic transit-times associated with the respective beam, the respective volumetric flow rate.

11. The method of claim 10 further comprising an additional step, executed before step (c), of calculating the diameter of the pipe from a respective measured transit-time associated with the respective beam.

12. The method of claim 10 wherein the at least one probe comprises two probes, the respective axis of each of the two probes having a separately selected angular setting with respect to the axis of the pipe; and wherein the step of calculating the volumetric flow rate comprises combining the respective volumetric flow rates to yield a composite volumetric flow rate.

13. The method of claim 12 wherein the two angular settings are selected to provide an angle of sixty degrees of arc between the axes of the two probes and wherein the respective volumetric flow rates are combined by averaging.

14. The method of claim 10 wherein one of the at least one probe respectively comprises two pairs of transducers, each pair defining a respective acoustic beam, wherein the acoustic beam associated with the first pair of transducers is reflected three times from the inside surface of the pipe and the beam associated with the second pair of transducers is reflected four times from the inside surface of the pipe.

15. The method of claim 10 wherein each of the transducers is arranged to transmit and receive respective acoustic signals perpendicular to the pipe axis, wherein the respective acoustic signals define respective beams having a selected angular dispersion, and wherein at least the dispersion and the respective flow measurement distance are selected so that the respective acoustic signal transmitted from said each transducer is received by the other transducer with which it is paired.

16. The method of claim 10 wherein one of the transducers is arranged to transmit and receive a respective acoustic signal at an acute angle to the flow measurement direction and that transducer with which it is paired is arranged to transmit and receive a respective acoustic signal at an obtuse angle that is ninety degrees of arc greater than the acute angle to the flow measurement direction.

17. A flow sensor for measuring a volumetric flow rate of a fluid flowing in a pipe, the sensor comprising: at least two probes insertable into the pipe to respectively selected insertion depths therein, each probe respectively comprising at least one pair of acoustic transducers spaced apart by a respective flow measurement distance along a respective flow measurement direction transverse to a respective probe axis, each pair of transducers arranged to transmit and receive respective oppositely directed acoustic signals transverse to the respective flow measurement direction; at least one signal processing circuit for energizing the transducers associated with at least one of the probes, for receiving respective transit-time signals from each pair of associated transducers and for generating therefrom at least one respective raw flow signal output responsive to a component of the fluid flow along the respective flow measurement direction; and a flow measurement circuit operable to receive a size signal value and the at least one raw flow signal and to calculate therefrom the volumetric flow rate.

18. The flow sensor of claim 17 wherein the at least one signal processing circuit is also operable to generate the size signal value.

19. The flow sensor of claim 17 comprising two probes inserted into the pipe so that an angle between the two probe axes is sixty degrees of arc.

20. The flow sensor of claim 17 wherein the at least two probes are spaced apart along the pipe.

21. The flow sensor of claim 17 comprising exactly two probes, each having a single respective pair of transducers mounted thereon, wherein the flow measurement circuit is operable to average the two electrical flow signals.

22. The sensor of claim 17 wherein at least one of the probes comprises two pairs of transducers, the two pairs spaced apart along the respective probe axis by a selected spacing.

* * * * *